United States Patent [19]

Tsujikawa et al.

[11] Patent Number: 4,909,790
[45] Date of Patent: Mar. 20, 1990

[54] LIQUID INFUSION DEVICE

[75] Inventors: Hajime Tsujikawa, Otsu; Toshiki Yoshida, Mishima, both of Japan

[73] Assignee: Nissho Corporation, Osaka, Japan

[21] Appl. No.: 200,987

[22] Filed: Jun. 1, 1988

[30] Foreign Application Priority Data

| Jun. 18, 1987 | [JP] | Japan | 62-152971 |
| Aug. 17, 1987 | [JP] | Japan | 62-204791 |
| Nov. 20, 1987 | [JP] | Japan | 62-294809 |

[51] Int. Cl.⁴ .............................................. A61M 5/00
[52] U.S. Cl. ................................ 604/132; 604/214; 222/212; 222/386.5
[58] Field of Search .......... 604/132, 135, 214; 222/107, 215, 212, 386.5

[56] References Cited

U.S. PATENT DOCUMENTS

| 515,288 | 2/1894 | Harsin | 604/132 |
| 1,098,222 | 5/1914 | Brasefield | 604/214 |
| 3,469,578 | 9/1969 | Bierman | 604/132 |
| 3,796,356 | 3/1974 | Venus | 222/212 |
| 3,961,725 | 6/1976 | Clark | 222/1 |
| 4,031,891 | 6/1977 | Jess | 604/126 |
| 4,121,585 | 10/1978 | Becker, Jr. | 604/86 |
| 4,140,117 | 2/1979 | Buckles et al. | 604/132 |
| 4,386,929 | 6/1983 | Peery et al. | 604/132 |
| 4,769,008 | 9/1988 | Hessel | 604/132 |

FOREIGN PATENT DOCUMENTS

| 0172586 | 8/1981 | European Pat. Off. |
| 1066739 | 2/1966 | United Kingdom |

Primary Examiner—Dalton L. Truluck
Attorney, Agent, or Firm—Armstrong, Nikaido Marmelstein, Kubovcik & Murray

[57] ABSTRACT

A liquid infusion device comprises a bladder assembly and a flow-regulating portion. The bladder assembly comprises a tubular outer shaft, an inner shaft slidably received within the outer shaft and a bladder covering the outer and inner shafts. The bladder can inflate in both its radial and axial directions whereby reducing the residual amounts of a liquid drug in the bladder on dispensation of the liquid drug. The flow-regulating portion comprises a pipe having at least one small hole or a pipe having a very small diameter, so that the accurate regulation of the liquid drug can be performed.

13 Claims, 10 Drawing Sheets

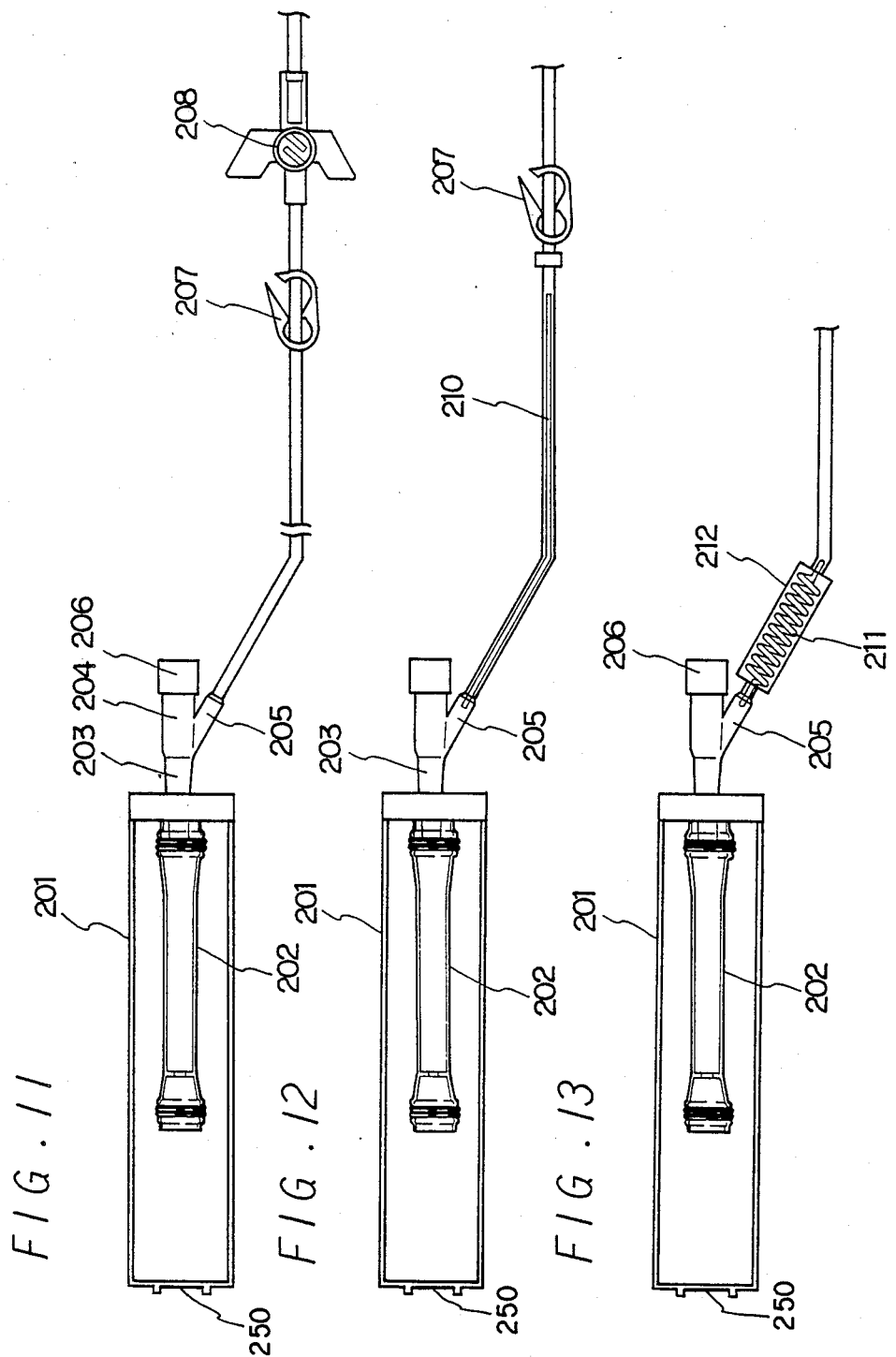

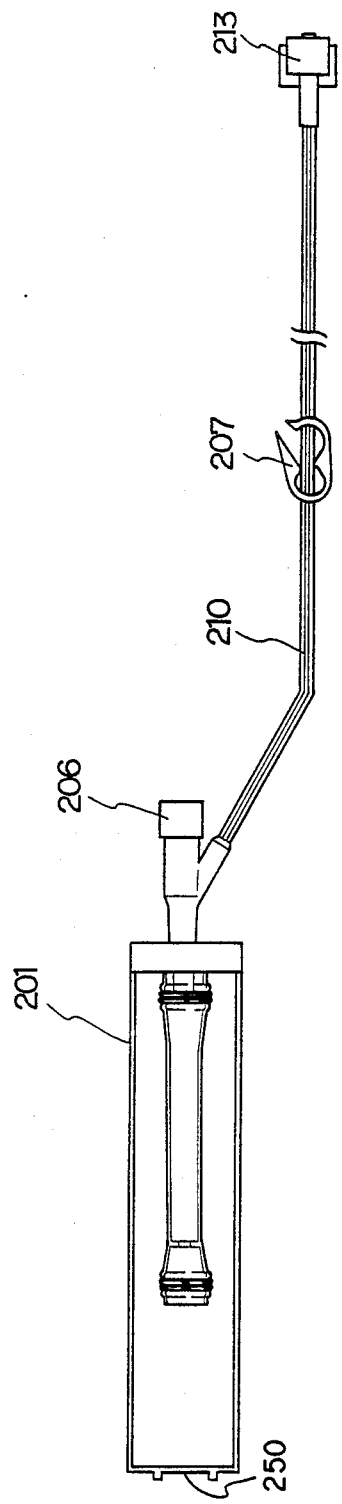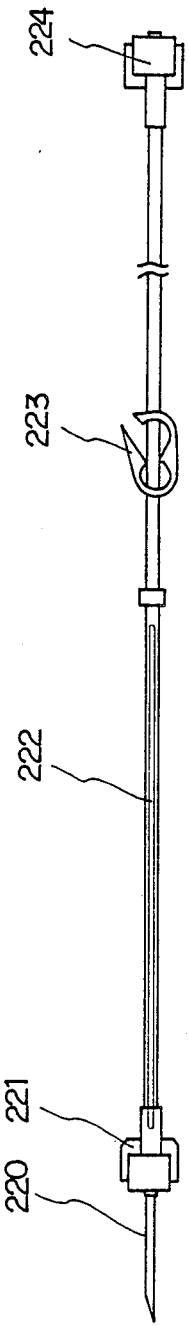
FIG. 14
FIG. 15

LIQUID INFUSION DEVICE

FIELD OF THE INVENTION

The present invention relates to a liquid infusion device used for continuously dispensing a predetermined amount of liquid drug little by little into a blood vessel, urinary bladder and the like, and more particularly to a liquid infusion device which is light in weight and easy to treat, capable of accurately regulating the flow rate of a liquid drug, and enables the liquid drug to be dispensed to some patients while allowing them to walk, when dispensing the liquid drug to the upper part of the body.

BACKGROUND OF THE INVENTION

Hitherto, as a device for dispensing a very small amount of a liquid drug such as antibiotics and a carcinostatic substance to a blood vessel, urinary bladder and the like, there is proposed an infusor of a liquid drug with a bladder (e.g. Japanese Unexamined Patent Publication No. 11465/1987) wherein the liquid drug is charged into the bladder made of elastic material and the liquid drug is dispensed into a blood vessel and the like for a relatively long period of time with the use of a shrinkage force of the bladder. The infusor described in the above publication has a constitution as shown in prior art FIG. 17. The liquid drug injected from an inlet portion 352 wherein a check valve 351 is mounted, is charged into a bladder 356 through an inlet port 354 made on a tubular body 353. In that case, an end portion of a tube 357 remaining within a blood vessel is stopped up with a hand, or a flow control valve 358 is throttled at its maximum, in order to prevent a flow-out of the liquid drug. After being charged in the bladder in a predetermined amount, the liquid drug is dispensed to the blood vessel by the shrinkage force of the bladder 356 through an outlet port 359, an outlet portion 360 and the tube 357. The publication describes that the above-mentioned infusor has a simpler structure than liquid-transfusing pumps and the like used before proposal of the infusor, and make the treatment thereof easy.

The infusor, however, has a problem in which fine flow regulation of liquid drug is difficult because the amount of liquid drug is effected by the sectional area of the outlet port 359, the throttle ratio of the flow control valve 358, the resistance of the pipe line of a catheter for the blood vessel connected to the infusor, and the like. Further, a considerable amount of the liquid drug remains within the tubular body 353 and the like without being dispensed to the human body, since the bladder 356 can deform only in a radial direction of the tubular body 353 (such a direction shown by X in FIG. 17).

U.S. Pat. No. 4,318,400 discloses a medical infusor having an elastomeric bladder in a housing wherein a piston mounted in the housing slides along an axis of the housing while contacting to an inner surface of the housing with the dispensation of the liquid drug in the bladder.

However, two shafts in the bladder are at both ends of the bladder when the liquid drug is charged therein, that is to say, two shafts are not interconnected, so that the bladder inflating into a cylindrical form is not supported in an axial direction of the housing. Therefore, a part of the bladder becomes bulb-shaped whereby generating a sudden rise of pressure in the bladder. Thus, the liquid drug in the bladder cannot be dispensed at a constant flow velocity.

Accordingly, it is an object of the present invention to provide a liquid infusion device capable of finely regulating the flow rate of the liquid drug, dispensing the liquid drug at a substantially constant flow velocity, and reducing the residual amounts of liquid drug in the bladder.

SUMMARY OF THE INVENTION

In accordance with the present invention, there is provided a liquid infusion device comprising;

a bladder assembly comprising a tubular outer shaft, an inner shaft slidably received within the outer shaft, a bladder made of elastic material placed outside the outer shaft and inner shaft, one end of the bladder being tightly fixed to the outer shaft and other end of the bladder being fixed to the inner shaft, and an inlet/outlet portion communicated to one end of the outer shaft;

a housing containing the bladder assembly, the inlet/outlet portion being communicated to the outer shaft on the end surface of the housing; and a flow-regulating portion comprising a pipe having at least one small hole or a pipe having an inner diameter of 10 to 500 $\mu$m.

BRIEF EXPLANATION OF THE DRAWINGS

FIGS. 11 to 15 are further embodiments of a liquid infusion device of the present invention.

DETAILED DESCRIPTION

Figure 1:
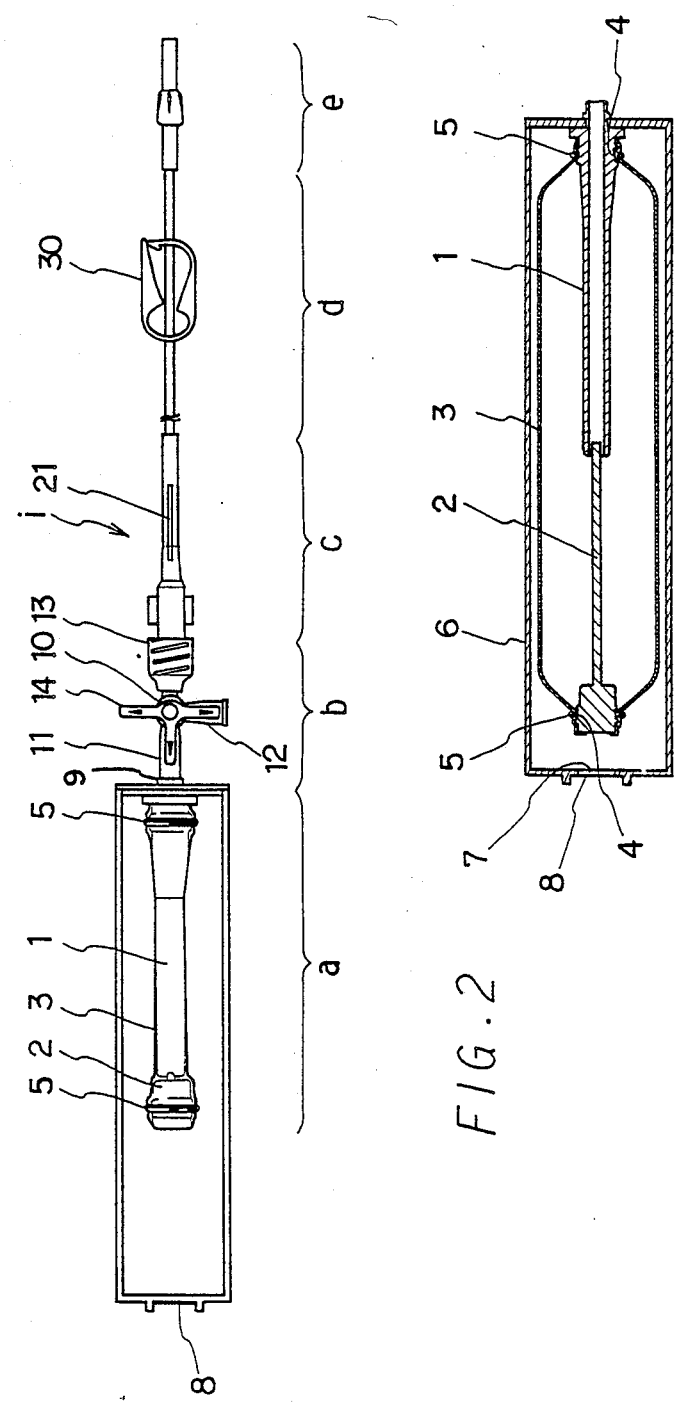
FIG. 1 is an explanatory view of an embodiment of a liquid infusion device of the present invention.

Referring now to the accompanying drawings, there is explained a liquid infusion device of the present invention. FIGS. 1 to 4 show an embodiment (first embodiment) of a liquid infusion device of the present invention.

In FIGS. 1 to 4, numeral i is an embodiment of a liquid infusion device of the present invention comprising a bladder assembly a, a cock portion b, a flow-regulating portion c, a tube d for dispensing the liquid drug, and a connector e.

The bladder assembly a is a portion for storing or containing the liquid drug therein and injecting the liquid drug to a predetermined portion of human body, and comprises a tubular outer shaft 1, an inner shaft 2 slidably received within the outer shaft 1, and a bladder 3 placed outside the outer shaft 1 and inner shaft 2. The outer shaft 1 and inner shaft 2 are made of synthetic resin such as polycarbonate, polyethylene, and polypropylene. The bladder 3 is made of elastic material such as silicone rubber, butyl rubber, nitryl butadiene rubber, poly-1,4-butadiene, polyisoprene, polyurethane, butadiene stylene copolymer, and natural rubber.

The bladder 3, having a tubular shape, is placed outside the outer shaft 1 and inner shaft 2 to cover both shafts. One end of the bladder 3 is airtightly fixed to the outer shaft 3 by a sealing means such as O-ring 5 while the other end of the bladder 3 is similarly fixed to the inner shaft 2. The O-rings 5 are seated within annular grooves 4 formed on the outer shaft 1 and inner shaft 2. The inside of the outer shaft 1, wherein the inner shaft 2 slides, serves as a passage for the liquid drug charged within the bladder 3 to a cock portion b. It is accordingly preferable to provide clearance of about 0.5 to 3mm between an inner surface of the outer shaft 1 and an outer surface of the inner shaft 2. The size and thickness of the bladder 3 are not particularly limited in the liquid infusion device of the present invention, therefore, bladders having various kinds of size and thickness can be applied to a liquid infusion device of the present invention depending on the amount of liquid drug dispensed to patients, dispensation time and the like. The employable values of outer diameter, thickness, and length thereof are about 2 to 30mm, 0.1 to 2.0mm, and 3 to 30cm, respectively. The bladder is inflatable in both the radial direction and the longitudinal direction (i.e. axial direction of the outer shaft 1 and inner shaft 2) by the charging of the liquid drug. The inner shaft 2 goes into or goes out from the outer shaft 1 with the movement of the bladder 3. An amount of liquid drug dispensed from the bladder 3 can be determined by marking with degrees at the surface of the inner shaft 2, since the relationship between position of the inner shaft 2 and an amount of liquid drug remained in the bladder 3 is constant.

Figure 2:
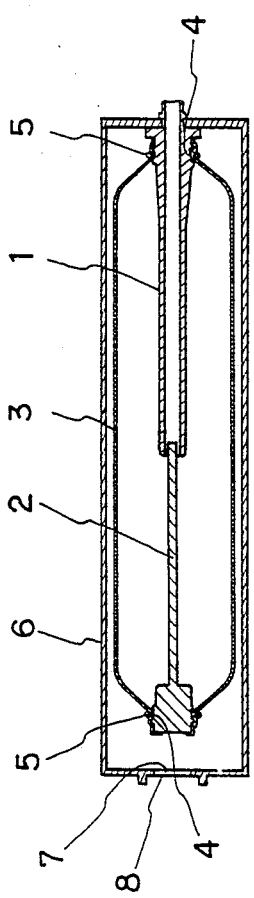
FIG. 2 is an enlarged sectional view of a bladder assembly of the liquid infusion device of FIG. 1 wherein liquid drug is charged in a bladder.

A housing 6 made of synthetic resin is, for example, a tubular shape, in which the bladder 3 is encased. A housing 6 is provided to prevent leakage of the liquid drug to the outside caused by damage to the bladder 3, which occurs by contacting with external sharp objects. It is preferable that the housing 6 is made of a transparent material to allow observation of the liquid drug dispensed with a naked eye from outside the housing 6. The size of the housing is determined depending on the size of the inflated bladder 3. In the embodiment of FIG. 2, there is a clearance between an inner surface of the housing 6 and the bladder 3, but it is not particularly necessary in the present invention. The inner diameter of the housing, from a viewpoint of miniaturization of a device, is preferably determined in a size that the inflated bladder 3 almost contacts with an inner surface of the housing 6. The housing 6 might be fixed to the outer shaft 1 or detachably mounted to the outer shaft 1. Numeral 9 is an inlet/outlet portion formed on an end surface of the housing 6 and communicating to one end of the outer shaft opposite to an end wherefrom the inner shaft is inserted.

There is formed an opening 7 for air vent at a suitable place of the housing 6. The opening 7 might be provided with a hydrophobic filter 8 allowing the passage of air while not allowing the passage of the liquid drug.

A cock portion b is provided to change the flow passage of the liquid drug, by which the liquid drug is determined to be charged or dispensed. A three-way cock 10 is used in the embodiment of FIG. 1. Other parts such as two-way cock and Y-shaped pipe can off course be used in the cock portion b. The cock portion b in FIG. 1 has an inlet portion 12 whereto the liquid drug is injected by the use of an injector and the like, a connecting portion 11 to be connected to the outer shaft 1, and an outlet portion 13 to be connected to a flow-regulating portion c. The change of passage of the liquid drug can be effected by the operation of a control 14. In the present embodiment, the outlet portion 13 is composed of a connection type of male and female luertaper. The cock portion b is attached to or detached from the flow-regulating portion c at this outlet portion 13.

Figure 3:
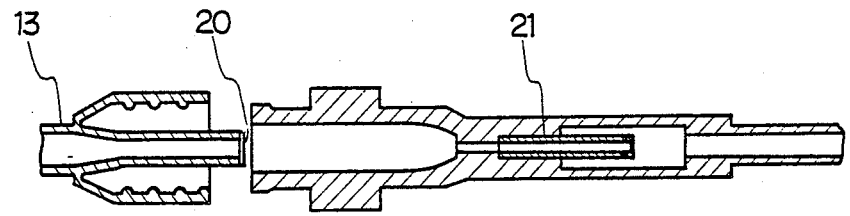
FIG. 3 is an enlarged sectional view of a flow-regulating portion of the liquid infusion device of FIG. 1.
Figure 4:
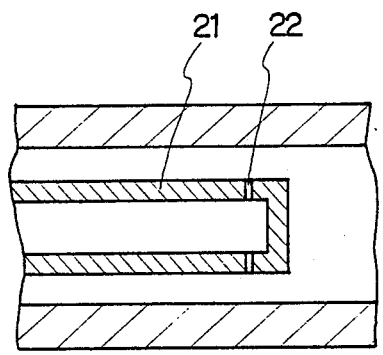
FIG. 4 is an enlarged sectional view of an end portion of the flow-regulating portion of FIG. 3.

The flow-regulating portion c regulates flow rate of the liquid drug. The flow regulation of the liquid drug is carried out by one or more than one small holes 22 made on the side portion of a stainless pipe disposed in the passage of liquid drug as shown in FIGS. 3 to 4. Though the diameter of small holes 22, which might be determined depending on the kind or flow rate of the liquid drug, is not particularly limited in the present invention, it is preferably about 20 to 100 μm. There are some cases that one small hole 22 can accurately regulate the flow rate of the liquid drug. It is, however, preferable in general to make a plurality of holes each having a diameter as small as possible, from a viewpoint of accurate flow regulation, particularly flow regulation of a liquid drug having a high viscosity.

In the liquid infusion device i of the present embodiment, there is provided a filter 20 made of synthetic resin such as nylon between the outlet portion 13 of the cock portion b and the pipe 21 in the flow-regulating portion c. As a material of the filter 20, there can be preferably used membrane filters such as a mesh filter and a filter composed of woven fabric or nonwoven fabric. Laminated filters composed of a sintered body of polypropylene can also be used. The hole diameter of the filter 20 is determined in consideration of the diameter of the small holes 22 made on the pipe 21 in the flow-regulating portion c. That is, the filter 22 is provided in order to prevent the flow of the liquid drug from stopping or becoming slow, resulting from being choked up with particles in the small holes 22 of the pipe 21. The flow rate of the liquid drug is entirely disturbed in the worst case. From this point of view, the hole diameter of the filter 20 is required to be smaller than that of the small holes 22 of the pipe 21. In the present embodiment, the pipe 21 having small holes is made of stainless steel. However, the pipe 21 might be made of other materials such as synthetic resin, for example, polycarbonate, polypropylene, ABS (acrylonitrilebutadiene-styrene) resin so long as they have chemical resistance, processability, non-toxicity and the like.

The filter 20 is provided, in the present embodiment, at an end of the outlet portion 13 of the cock portion b. However, the position of the filter 20 is not limited to such a position as disclosed in the present embodiment, and the filter 20 can be provided, as described above, at a suitable position between the outlet portion 13 and the pipe 21.

A tube d for dispensing liquid drug made of soft synthetic resin such as soft polyvinyl chloride, polypropylene and polyethylene is connected to the flow-regulating portion c at its human body side. The inner diameter, thickness and length of the tube d might be determined in consideration of an amount of liquid drug or use of a liquid infusion device. When a mini clamp 30 is provided at a midway of the tube d, the dispensation of the liquid drug can be easily stopped or reopened.

A Luer-tapered connector e is attached to the end of the tube d. Through the connector e, vein needle or PSV (Pediatric Skelton Vein) assembly is connected to the tube d. A check valve (not shown) might be mounted in the connector e to prevent a back flow of the liquid drug due to vein pressure.

Next, there is explained a use of the first embodiment of a liquid infusion device of the present invention.

The injection of liquid drug is carried out by inserting a injector and the like (not shown) into the opening of the inlet portion 12 of cock portion b. In that case, the three-way cock 10 is operated to allow the liquid drug to flow into the bladder 3. With the charging of the liquid drug, the bladder 3 inflates in its radial direction and axial direction. After a predetermined amount of liquid drug is charged into the bladder 3, the three-way cock 10 is operated to communicate the bladder a with the flow-regulating portion b. Thereafter, the injector is pulled out from the opening of the inlet portion 12. When the three-way cock 10 is operated after the charging of the liquid drug, the mini clamp is required to be closed so as to prevent back flow of the liquid drug toward the tube c. Then, the liquid infusion device is connected, through the connector, to a PSV assembly or a bladder catheter according to portions of the human body to be dispensed with the liquid drug. The dispensation of the liquid drug into the human body of a patient is carried out after a prescribed operation such as an air vent.

Figure 5:
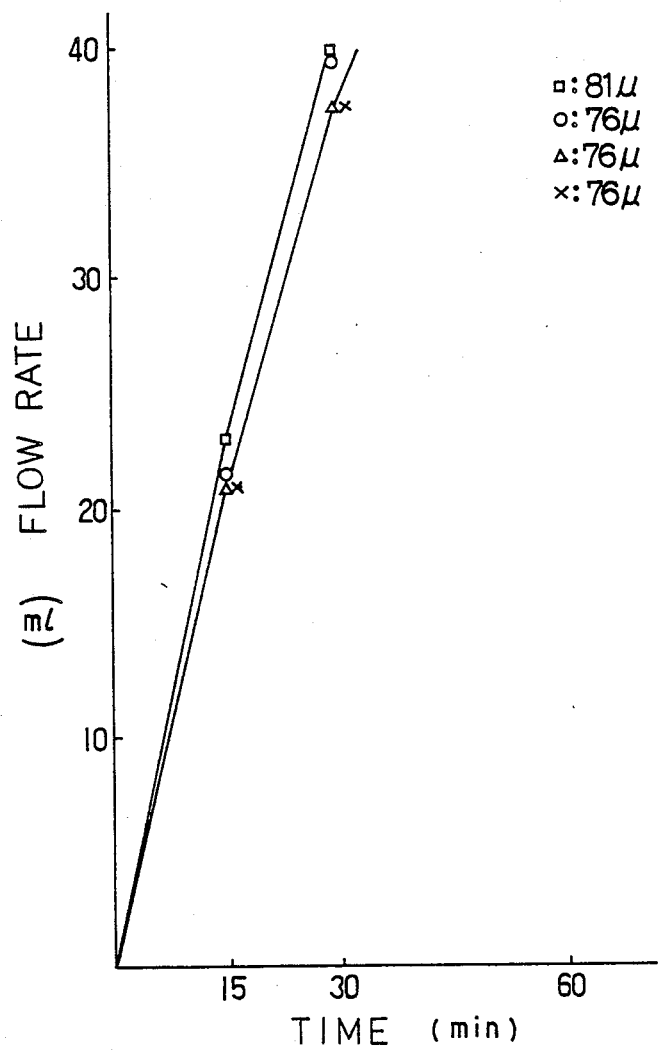
FIG. 5 is a graph showing flow characteristic of an embodiment of a liquid infusion device of the present invention.

FIG. 5 is a graph showing a flow characteristic of a liquid infusion device according to the present embodiment, wherein 40 ml of physiological saline solution (concentration: 0.9% NaCl) was charged into a bladder and a relationship between dispensation time and dispensation amount was measured with the change of diameter of the small hole of a pipe in the flow-regulating portion. The measurement was carried out at a room temperature. FIG. 5 shows that the flow rate of the liquid drug of the liquid infusion device of the present embodiment is stable, that is to say, the flow rate of the liquid drug presents a good linearity.

Next there is explained another embodiment (second embodiment) of a liquid infusion device of the present invention based on FIGS. 6 to 10.

Figures 6, 7:
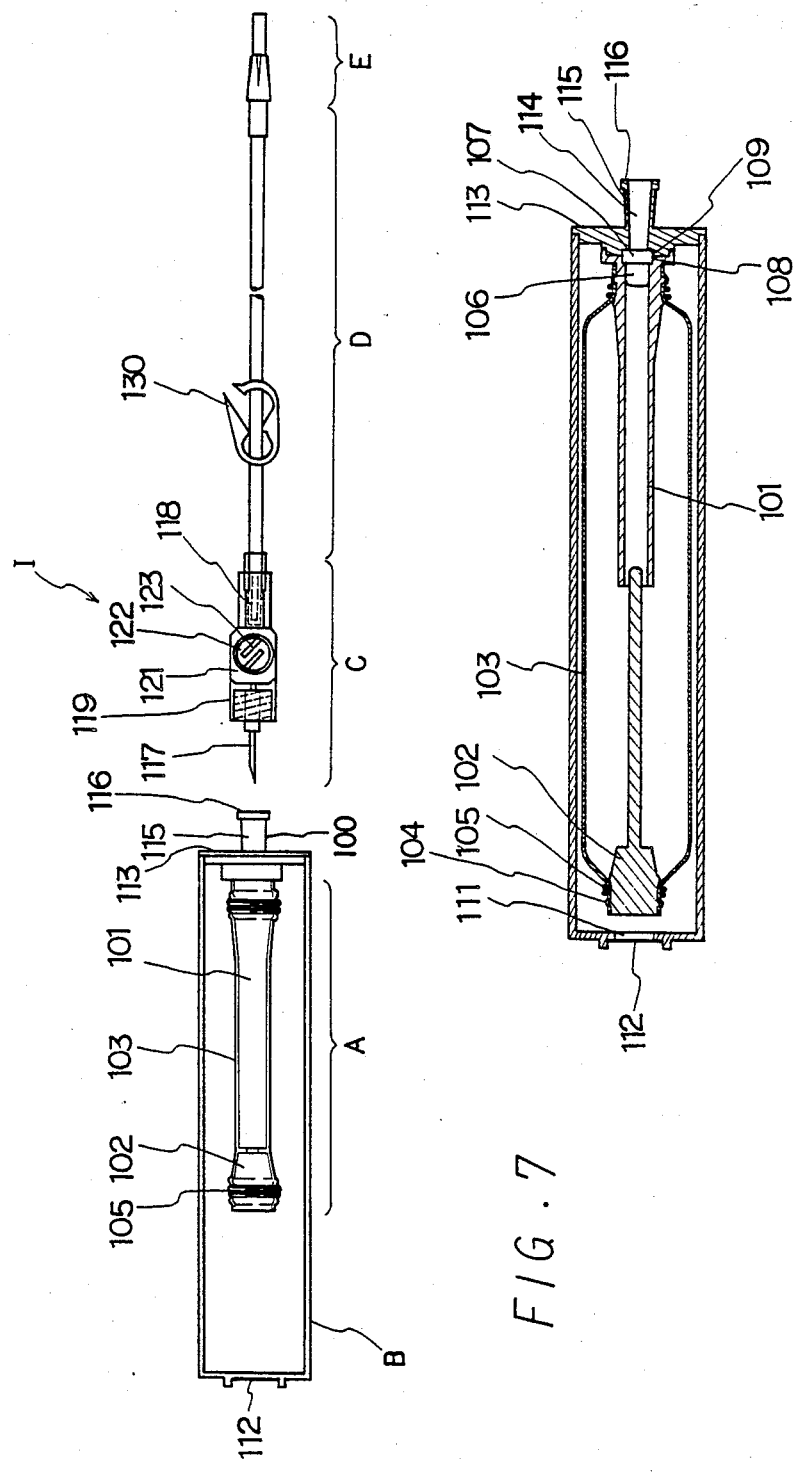
FIG. 6 is an explanatory view of another embodiment of a liquid infusion device of the present invention wherein an injection needle is not pricked into an injection plug.
FIG. 7 is an enlarged sectional view of a bladder assembly of the liquid infusion device of FIG. 6 wherein the liquid drug is charged in a bladder.

FIG. 6 is an explanatory view of another embodiment of a liquid infusion device of the present invention wherein a needle for the liquid drug injection is not pricked into an injection plug.

FIG. 7 is an enlarged sectional view of a bladder assembly of the liquid infusion device of FIG. 6 wherein the liquid drug is charged in a bladder.

Figure 8:
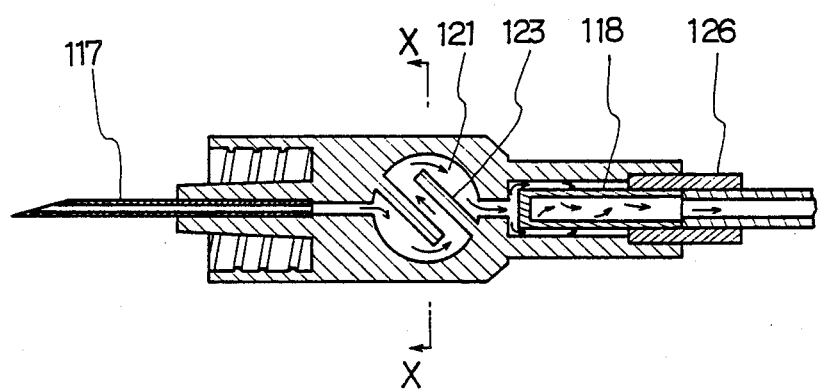
FIG. 8 is an enlarged sectional view of a flow-regulating portion of the liquid infusion device of FIG. 6.

FIG. 8 is an enlarged sectional view of a flow-regulating portion of the liquid infusion device of FIG. 6.

Figure 9:
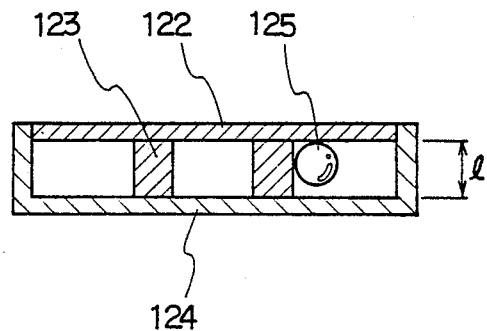
FIG. 9 is a schematic sectional view taken along the line X—X of FIG. 8.

FIG. 9 is a schematic sectional view taken along the line X—X of FIG. 8.

In FIGS. 6 to 9, numeral I is a liquid infusion device according to another embodiment of the present invention. The liquid infusion device I comprises a bladder assembly A, a housing B, a flow-regulating portion C, a tube D for dispensing liquid drug, and a connector E.

The bladder assembly A is a portion for storing or containing the liquid drug therein and injecting the liquid drug to a predetermined portion of the human body, and comprises a tubular outer shaft 101, an inner shaft 102 slidably received within the outer shaft, a bladder 103 placed outside the outer shaft 101 and inner shaft 102, and a plug 106 inserted into an open end of the outer shaft 101 for injecting the liquid drug into the bladder. The outer shaft 101, inner shaft 102 and bladder 103 are made of materials as described relating to the first embodiment, respectively.

The bladder 103, having a tubular shape, is placed outside the outer shaft 101 and inner shaft 102 to cover both shafts. One end of the bladder 103 is airtightly fixed to the outer shaft 101 by a sealing means such as O-ring 105 while the other end of the bladder 103 is similarly fixed to the inner shaft 102. The O-rings 105 are seated within annular grooves 104 formed on the outer shaft 101 and inner shaft 102. The inside of the outer shaft 101 serves as, not only providing a flow passage for the liquid drug filled in the bladder 103 to a flow-regulating portion c, but also allowing the slide of inner shaft 102. It is accordingly preferable to provide clearance of about 0.5 to 3mm between an inner surface of the outer shaft 101 and an outer surface of the inner shaft 102. The size and thickness of the bladder 103 are not particularly limited in the liquid infusion device of the present invention. Therefore, bladders having various kinds of size and thickness can be applied to liquid infusion devices of the present invention according to an amount of the liquid drug dispensed to patients, dispensing time and the like. The employable values of outer diameter, thickness, and length thereof are about 2 to 30mm, 0.1 to 2.0mm, and 3 to 30cm, respectively.

The bladder is inflatable in both the radial direction and longitudinal direction (i.e. axial direction of the outer shaft 101 and inner shaft 102) by the charging of the liquid drug. The inner shaft 102 goes into or goes out from the outer shaft 101 with the movement of the bladder 103. An amount of the liquid drug dispensed from the bladder 103 can be determined by marking with degrees on the surface of the inner shaft 102, since the relationship between position of the inner shaft 102 and an amount of the liquid drug remaining in the bladder 103 is constant.

A plug 106 is airtightly and liquidtightly inserted into an end of the outer shaft 101 (such an end opposite to the end whereinto the inner shaft 102 is inserted) and is used for injecting the liquid drug into the bladder. The plug 106 is made of the rubber-like elastic material such as silicone rubber and has a superior prick resistance. In the specification the term "prick resistance" means a property which keeps liquid-tightness even if pricked with an injection needle many times, and which prevents the liquid drug from leaking into the bladder. The plug 106 shown in FIGS. 6 to 7 has a head 107. Stepped portions 108, 109 are formed on the end of the outer shaft 101 and the end surface of a housing B respectively. The head 107 of the plug 106 is fixed by the above-mentioned stepped portion 108, 109, so that slippage or coming out of the plug 106 is prevented when pricking the plug with a needle or pulling the needle out to inject or dispense the liquid drug. The fixation of the plug 106 can be carried out by the use of adhesives.

The housing B serves not only to prevent damage of the bladder 103 from contact with external sharp objects but also to seal the liquid drug so as not to disperse out when it leaks out from the bladder because of defects of the bladder such as a pinhole. The housing B is preferably made of synthetic resin such as polyvinyl chloride, polypropylene and polycarbonate. The shape of the housing B is not limited in the present invention. The housing sufficiently serves as a protector in any shape such as tubular or rectangular if it is large enough to contain the inflated bladder 103 therein. It is preferable that the housing 106 is made of a transparent material to allow observation of the liquid drug dispensed with the naked eye from outside the housing 106.

The size of the housing is determined depending on the size of the inflated bladder 103. In the embodiment of FIG. 7, there is a clearance between an inner surface of the housing 106 and the bladder 103, but it is not particularly necessary in the present invention. The inner diameter of the housing, from a viewpoint of miniaturization of a device, is preferably determined to be a size that the inflated bladder 103 almost contacts with an inner surface of the housing B. Numeral 100 is an inlet/outlet portion formed on an end surface of the housing B and communicating to one end of the outer shaft opposite to an end wherefrom the inner shaft is inserted.

As described above, the housing B covers the bladder assembly A in a sealed condition to prevent leakout of the liquid drug even if the bladder is damaged. A disadvantage, arises however, if the inside of the housing B is perfectly kept airtight, because air pressure in the housing B becomes high with the injection of the liquid drug into the bladder 103 so that the injection of the liquid drug beyond some volume becomes impossible. To avoid the above disadvantage, there is formed an opening for an air vent at a suitable place of the housing B in the liquid infusion device of the present invention. A hydrophobic filter, which allows passage of air but not the liquid drug, is provided at the opening. In the embodiment shown in FIGS. 6 to 7, the opening 111 is formed at an end surface of the housing B. The hydrophobic filter 112 is so provided at the housing B to cover the opening 111. When determining materials of the hydrophobic filter 112, it should be taken into consideration that the liquid drug in the bladder 103 does not leak out from the housing B even if the bladder is damaged and air in the housing B is discharged with the inflation of the bladder 103 when the liquid drug is injected into the bladder 103. Polyester, Teflon and the like are preferably employed.

A hole 114 used for inserting an injection needle thereinto is formed on the end plate 113 of the housing B whereto the end of outer shaft 101, into which the plug is inserted, is attached. The hole 114 is formed to be coaxial with the outer shaft 101 and inner shaft 102, accordingly coaxial with the plug 106. Only a part of the head 107 of the plug 106 faces the outside through the hole 114 (the other portion of the head 107 is set in the annular groove defined by the stepped portions 108, 109). The formation of the hole 114 can be omitted provided that the end plate 113, to which the head 107 of the plug 106 contacts, is made of materials having a superior prick resistance as stated above.

On the end plate 113 of the housing B having the hole 114, there is formed an approximately tubular projection 115 coaxial with the hole 114. The projection 115 has a flange 116 to be connected to an end of a flow-regulating portion C described hereinafter. The formation of the projection 115 can serve to certainly prevent the liquid drug from touching an operator's hands and the like even if the liquid drug stains the surface of the head 107 of the plug 106 when injecting the liquid drug into the bladder 103. The connection between the housing B and the flow-regulating portion C can be carried out by pricking the plug 106 with a needle. It is preferable, however, that the projection 115 is engaged with or screwed into the end portion 119 of the flow-regulating portion.

The flow-regulating portion C serves to regulate the flow rate of the liquid drug. The control is carried out by making all of the liquid drug pass through at least one small hole made on a pipe provided in the passage of the liquid drug. A needle 117 for liquid drug injection is attached to one end of the flow-regulating portion C. Liquid drug charged previously in the bladder is guided to the flow-regulating portion C by pricking the needle 117 into the plug 106.

As a pipe having small holes, there can be employed the above mentioned pipe which has an end portion at a lower part for the liquid drug closed (see FIGS. 3 to 4), or other pipes having small holes such as a porous glass pipe.

Firstly, there is explained a pipe which has an end portion, at a lower part for the liquid drug, closed with reference to FIGS. 3 to 4.

In the embodiment, the liquid drug flows into a tube for the liquid drug dispensation described hereinafter through small holes.

Though the diameter of small holes, which might be determined depending on the kind or flow rate of the liquid drug, is not particularly limited in the present invention, it is preferably about 20 to 100 $\mu$m. There are some cases that one small hole can accurately regulate the flow rate of the liquid drug. It is, however, preferable in general to make a plurality each having holes of a diameter as small as possible, from a viewpoint of accurate flow regulation, particularly in the case of flow regulation of the liquid drug having a high viscosity. When using the above-mentioned pipe, it is necessary to provide a filter 150 made of synthetic resin such as nylon between the needle 117 and the pipe in the flow-regulating portion C. As a material of the filter 20, there can be preferably used membrane filters such as a mesh filter and a filter composed of woven fabric or nonwoven fabric. Laminated filters composed of a sintered body of polypropylene can also be used. The diameter of the filter is determined in consideration of the diameter of the small holes made on the pipe in the flow-regulating portion C. That is, the filter is provided in order to prevent the flow of the liquid drug from stopping or becoming slow, resulting from being choked up with the particles in the small holes of the pipe. The flow of the liquid drug is entirely disturbed in the worst case. From this point of view, the diameter of the filter is required to be smaller than that of the small holes of the pipe. In the present embodiment, the pipe whereon small holes are made is made of stainless steel. However, the pipe might be made of other materials such as synthetic resin, for example, polycarbonate, polypropylene, ABS resin so long as they have chemical resistance, processability, non-toxicity and the like.

Next there is explained a porous glass pipe based on FIGS. 8 to 9. A porous glass pipe 118 is produced by, for example, forming borosilicate glass into a pipe by conventional methods, phase-partially-separating glass by heat treatment at a temperature of about 600° C., and giving acid treatment to a glass pipe. The obtained pipe has heat resistance and chemical resistance, and a large number of small holes having substantially equal diameter of about 0.1 to 0.3 μm at its side portion.

The length and inner diameter of the pipe are not particularly limited in the present invention. Accordingly they might be suitably determined depending on the flow rate or viscosity of the liquid drug. They are preferably about 2 to 20mm and about 0.5 to 5mm, more preferably about 5 to 15mm and about 1 to 3mm, respectively. Preferable thickness of the pipe is about 0.5 to 5mm. When using the above-mentioned porous glass pipe, accuracy of flow regulation can be much improved in comparison with the stainless pipe having small holes. That is, the possible lowest limit of a hole's diameter is about 15 μm when making holes on the pipe, so that the number of holes are limited. Accordingly the flow rate of the liquid drug becomes unstable due to clogging of a part of the small holes by impurities residing between the filter and the small holes. On the contrary, when using a porous glass pipe, the flow rate does not become unstable by a certain degree of clogging since a great number of holes are made on the side of a pipe.

In the case of porous a glass pipe, the flow of the liquid drug is disturbed by a so-called air-blocking phenomenon (such an phenomenon that air cannot enter small holes because of the surface tension of the liquid drug filling the small holes, so that the flow of the liquid drug is disturbed by the air remaining around the entrance of the small holes) if the liquid drug contains air bubbles therein. It is preferable to provide an air-venting portion 121 having a hydrophobic filter for an air vent at an upper stream of the porous glass pipe in order to prevent the above phenomenon.

An embodiment of the air-venting portion 121 is explained hereinafter based on FIGS. 8 to 9. In the embodiment of FIG. 8, the air-venting portion 121 is composed of a short column-like space. A filter 122 for the air vent comprises a hydrophobic filter and is provided at one-sided surface (such a surface as appears in FIG. 8) of a short column. The filter is depicted to be transparent for the sake of clear understanding of the drawing. Numeral 123 are baffle plates provided within the air-venting portion 121 to contact with the filter 122 and a bottom face of the flow-regulating portion C defining the short column-like space (see FIG. 9). The direct arrival of the liquid drug passing through the needle 117 to the porous glass pipe 118 can be avoided, because the liquid drug advance in the S-shaped locus along the baffle plates as shown by the arrow-mark in FIG. 8. Bubbles contained in the liquid drug is discharged out through the air-venting filter 122 while the liquid drug moves along baffle plates (see FIG. 9). It is preferable that the distance l between the air-venting filter 122 and a bottom face of the flow-regulating portion is as short as possible to ensure contact of the small bubbles with the filter 122. Concretely speaking, the distance is preferably 0.05 to 1.0mm, more preferably 0.1 to 0.5mm. The arrangement of baffle plates 123 is not limited to that shown in FIGS. 8 to 9, so long as the liquid drug does not easily reach the porous glass pipe. The shape of filter 122 and that of air-venting portion 121 are also not limited to those shown in the present embodiment and therefore might be suitably determined.

The porous glass pipe 118 and a tube D for liquid drug dispensation are connected and fixed to each other by means of a fixing member 126.

In the present embodiment, a tube D for dispensing the liquid drug made of soft synthetic resin such as soft polyvinyl chloride, polypropylene and polyetylene is connected to the flow-regulating portion C at its human body side. The inner diameter, thickness and length of the tube D might be determined in consideration of an amount of the liquid drug or use of a liquid infusion device. When a mini clamp 130 is provided at a midpoint of the tube D, the dispensation of the liquid drug can be easily stopped or reopened. A tapered connector E is attached to the end of the tube D. Through the connector E, vein needle or PSV assembly is connected to the tube D. A check valve (not shown) might be mounted in the connector to prevent a back flow of the liquid drug due to vein pressure.

Next, there is explained a use of the second embodiment of a liquid infusion device of the present invention.

The injection of the liquid drug is carried out by inserting a injector and the like (not shown) into the hole 114 and pricking the plug 106 with the injector. With the charging of the liquid drug, the bladder 103 inflates in its radial direction and axial direction. After a predetermined amount of the liquid drug is charged into the bladder 103, the injector is pulled out from the plug 106. In that case, the operator's hand and the like does not touch the liquid drug even if the liquid drug stains the head 107 of the plug 106, because the head 107 is placed at a sequestered position.

Next the plug 106 is pricked with the needle 117 of the flow-regulating portion C. In that case, the mini clamp is required to be closed so as to prevent back flow of the liquid drug toward the tube C. Then, the liquid infusion device is connected, through the connector, to a PSV assembly or a bladder catheter according to portions of the human body to be dispensed with the liquid drug. The dispensation of the liquid drug into the body of a patient is carried out after a prescribed operation such as an air vent.

Figure 10:
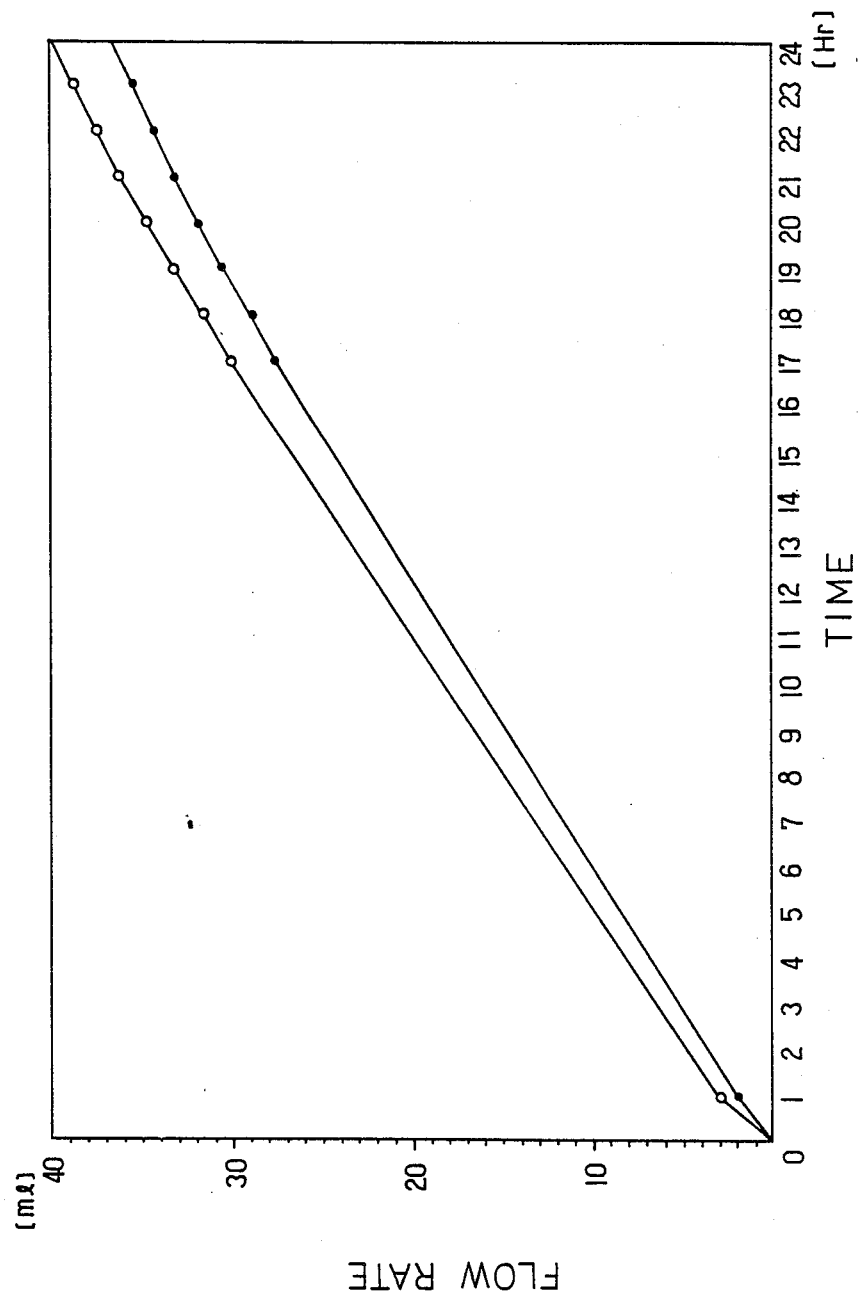
FIG. 10 is a graph showing a flow characteristic of another embodiment of a liquid infusion device of the present invention.

FIG. 10 is a graph showing a flow characteristic of a liquid infusion device according to the present embodiment, wherein 40ml of physiological saline solution (concentration: 0.9% NaCl) was charged into a bladder and a relationship between dispensation time and dispensation amount was measured. In FIG. 10, symbol O shows the flow characteristic of a liquid infusion device according to the second embodiment employing a porous glass pipe having small holes of which the average hole diameter is 0.22 μm at the flow-regulating portion. The outer diameter and inner diameter of the pipe are 3.0mm and 2.0mm, respectively. Symbol shows a flow characteristic of a liquid infusion device according to the first embodiment employing a stainless pipe having a small hole of 60 μm in hole diameter at the flow-regulating portion. The outer diameter and inner diameter of the pipe are 0.9mm and 0.6mm, respectively. The measurement was carried out at room temperature.

FIG. 11 is an explanatory view showing a further embodiment (third embodiment) of a liquid infusion device of the present invention. A connector 203 fixed to a housing 201 communicates with a bladder 202 and a branch tube having an outlet route 205 for the liquid drug. At the end of the inlet route 204, there is provided a plug 206 enabling the injection of the liquid drug into the bladder 202 with the use of an injector and the like. On the other hand, at the end of the outlet route 205, there is connected a tube having a clamp 207 capable of stopping the flow of the liquid drug at any time and at any position, and a flow-regulating portion 208. The liquid drug is dispensed into a body through an injector and the like.

FIG. 12 is an explanatory view showing still a further embodiment (fourth embodiment) of a liquid infusion device of the present invention wherein a flow-regulating portion 208 comprises a pipe 210 having a very small inner diameter. The pipe 210 might be made of, for example, metal or synthetic resin. The inner diameter of the pipe 210 is preferably from 10 to 500 $\mu$m, more preferably from 50 to 200 $\mu$m. When the inner diameter of the pipe 210 is less than 10 $\mu$m, the flow of the liquid drug is likely to be stopped because of the intermixed air in the liquid drug. On the other hand, when it is more than 500 $\mu$m, the flow regulation of the liquid drug is likely to become difficult. The length of the pipe 210 is preferably from 1 to 3,000mm, more preferably from 10 to 500mm. When the length of the pipe is less than 1mm, the flow regulation of the liquid drug is likely to become difficult. On the other hand, when it is more than 3,000mm, the size of a device is likely to become too large.

FIG. 13 is an explanatory view showing another embodiment (fifth embodiment) of a liquid infusion device of the present invention wherein a flow-regulating portion comprises an elastic spring-shaped pipe 211, for example made of stainless steel, instead of a pipe extending longitudinally shown in FIG. 12. The pipe 211 is encased with a casing 212, so that the flow-regulating portion is miniaturized.

FIG. 14 is an explanatory view showing a further embodiment (sixth embodiment) of a liquid infusion device of the present invention wherein a clamp 207 is provided at a suitable position of a pipe 210. In FIG. 14, numeral 213 is a connector whereto an injector and the like is connected. In FIGS. 11–14, numeral 250 shows a hydrophobic filter having the same function as the hydrophobic filter 8, 112 found in FIGS. 1 and 6.

FIG. 15 is an explanatory view showing still further embodiment (seventh embodiment) of a liquid infusion device of the present invention wherein a pipe 222 having a very small diameter is employed in the flow-regulating portion of a liquid infusion device of FIG. 6 instead of a porous glass pipe. Numeral 220 is a needle for injection to be pricked into a plug 106 fixed to a housing B. Numeral 221 is an end portion to be engaged with or screwed into a projection 115 of the housing B. A flow-regulating portion comprises a pipe 222 having a very small diameter. A clamp 223 capable of stopping the flow of the liquid drug is provide at a tube connected to the flow-regulating portion. Numeral 224 is a connector whereto an injector and the like for dispensing the liquid drug into a body is connected.

Figure 16:
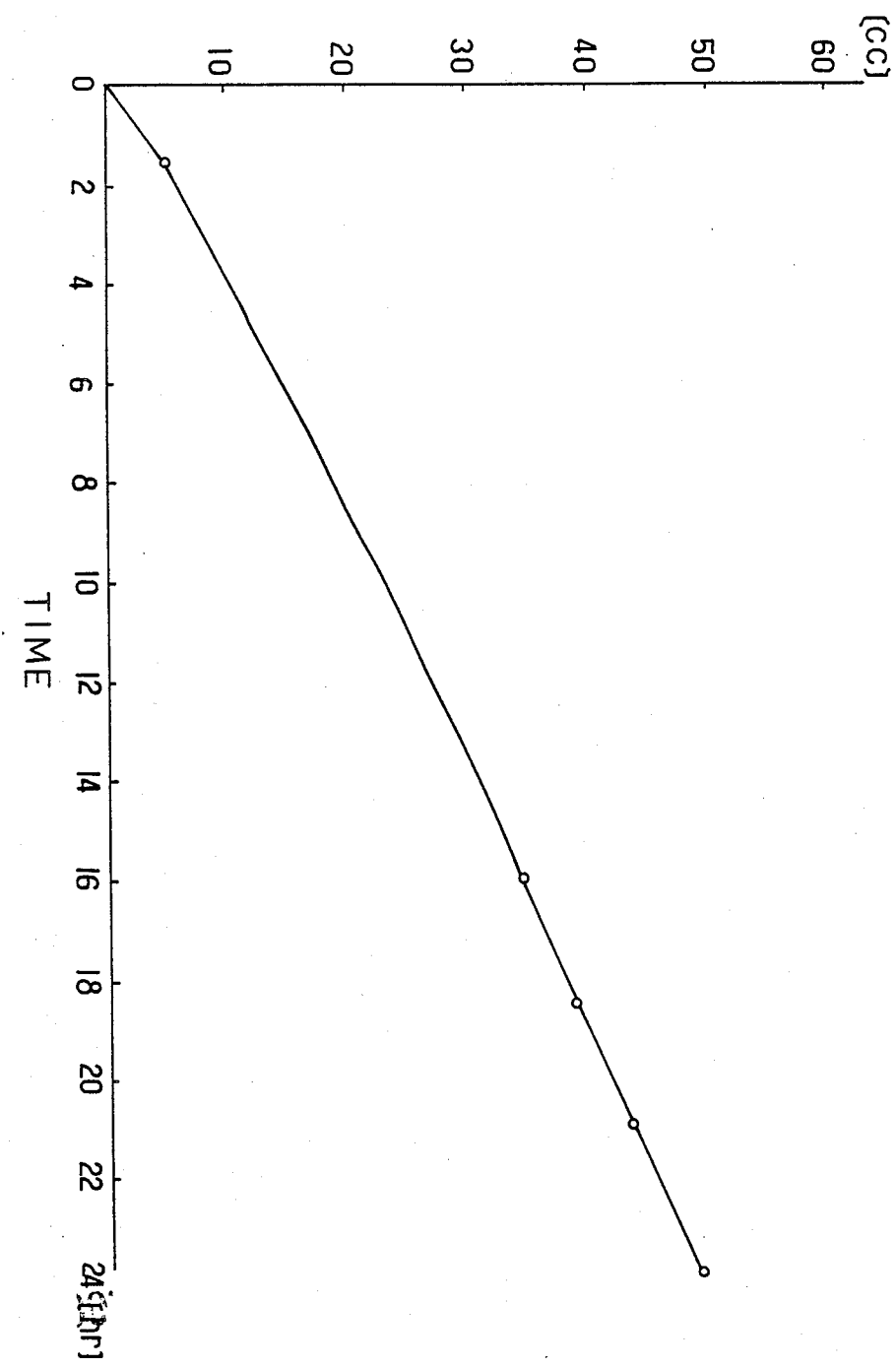
FIG. 16 is a graph showing a flow characteristic of still another embodiment of a liquid infusion device of the present invention.
Figure 17:
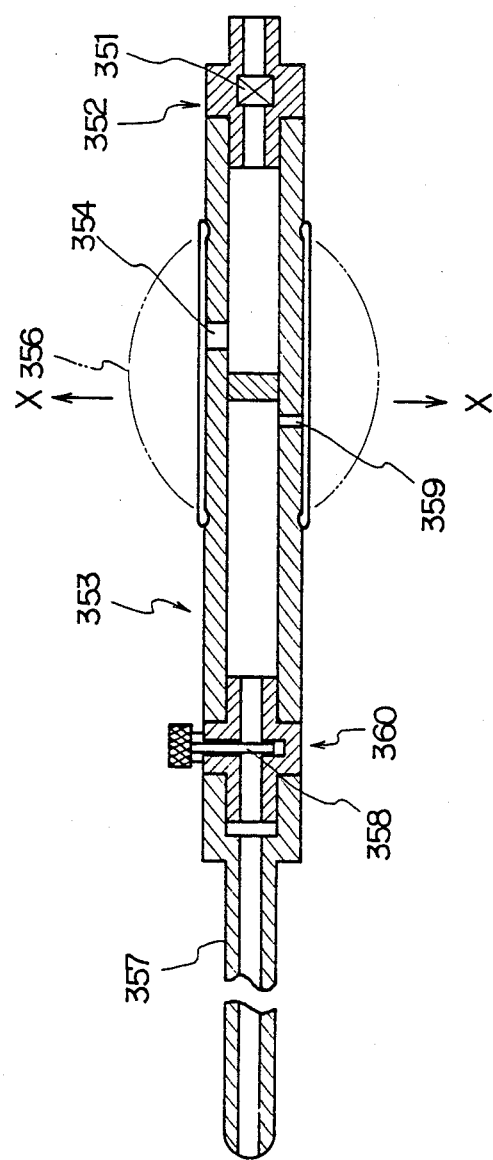
FIG. 17 is a longitudinal sectional view of a conventional liquid infusion device.

FIG. 16 is a graph showing a flow characteristic of a liquid infusion device according to the embodiment shown in FIG. 12, wherein 50ml of physiological saline solution (concentration: 0.9% NaCl) was charged into a bladder and a relationship between dispensation time and dispensation amount was measured. In FIG. 16, symbol O shows a flow characteristic of a liquid infusion device according to the embodiment employing a stainless pipe having a very small diameter. The outer diameter, inner diameter and length of the pipe are 0.3mm, 0.1mm and 230mm, respectively. The measurment was carried out at room temperature.

As stated above, the following effects can be obtained according to a liquid infusion device of the present invention.

(1) The accuracy of the flow rate of the liquid drug can be remarkably improved since the liquid drug is dispensed through small holes formed on the side of a pipe or through a tube having a very small diameter.

(2) A bladder is tightly fixed to an outer shaft and an inner shaft slidably received within the outer shaft, so that the bladder can inflate in its radial direction as well as in its axial direction. The residual amounts of the liquid drug in the bladder can be reduced extremely, because the inner shaft is guided by the outer shaft and the bladder can perfectly return into its uninflated shape.

(3) Leaking of the liquid drug is prevented by charging or discharging the liquid drug through a plug. Even if the liquid drug stains the surface of the plug after injection of the liquid drug into a bladder, there is not a danger of touching the liquid drug and the like because the plug is placed at a sequestered position not facing directly outside.

(4) When employing a porous glass pipe at a flow-regulating portion, the possibility of unstableness in the flow due to clogging is lessened in comparison with a pipe having small holes at its side portion, further improving accuracy of the flow of the liquid drug.

(5) A liquid infusion device of the present invention is light in weight and easy to treat. A patient can walk with a housing in his pocket and dispensing the liquid drug, so that the freedom of the patient's action is improved.

What we claim is:

1. A liquid infusion device comprising:
   a bladder assembly including
   a tubular outer shaft,
   an inner shaft slidably received within the outer shaft,
   a bladder made of elastic material placed outside the outer shaft and inner shaft, one end of said bladder being tightly fixed to the outer shaft and another end of said bladder being fixed to the inner shaft, said inner shaft sliding within the outer shaft based upon an amount of liquid in the bladder, and
   an inlet/outlet portion communicated to one end of the outer shaft opposite to an end wherefrom the inner shaft is inserted, said inlet/outlet portion allowing the liquid into and out of said bladder;
   a housing containing the bladder assembly, the inlet/outlet portion being communicated to the outer shaft on an end surface of the housing;
   a hydrophobic filter being provided at a wall surface of said housing; and
   a flow-regulating portion including a pipe having at least one small hole, said flow-regulating portion being attached to the end surface of the housing.

2. The device of claim 8, wherein a hydrophobic filter is provided at a wall surface of the housing.

3. The device of claim 1, wherein the device further includes a cock portion capable of changing a flow passage of liquid drug on charging or discharging liquid drug, and a filter provided between an outlet of the cock portion and the pipe in the flow-regulating portion.

4. The device of claim 1, wherein the inlet/outlet portion fixed to the housing communicates with a branch tube having two routes wherein a plug for liquid drug injection capable of being pricked with a needle is provided at an end of one route, and a flow-regulating portion and a clamp for stopping the flow of liquid drug at any time are connected to the other route for dispersing the liquid drug.

5. The device of any one of claims 1, wherein the inlet/outlet portion comprising a plug for liquid drug injection, and the device further includes a needle to be pricked into the plug.

6. The device of claim 5, wherein an approximately tubular projection having a flange substantially coaxial with the plug is formed on an end plate of the housing whereto the plug is attached, the projection being engaged with or screwed into an end portion of the flow-regulating portion whereat the needle for liquid drug injection is provided.

7. The device of claim 1, wherein an air-venting portion having an air-venting filter comprising a hydropholic filter is provided at an upper stream of the flow-regulating portion.

8. A liquid infusion device comprising:
a bladder assembly including
a tubular outer shaft,
an inner shaft slidably received within the outer shaft,
a bladder made of elastic material placed outside the outer shaft and inner shaft, one end of said bladder being tightly fixed to the outer shaft and another end of said bladder being fixed to the inner shaft, said inner shaft sliding within the outer shaft based upon an amount of liquid in the bladder, and
an inlet/outlet portion communicated to one end of the outer shaft opposite to an end wherefrom the inner shaft is inserted, said inlet/outlet portion allowing the liquid into and out of said bladder;
a housing containing the bladder portion, the inlet/outlet portion being communicated to the outer shaft on an end surface of the housing; and
a flow-regulating portion including a pipe having an inner diameter of 10 to 500 $\mu$m and a length of 1 to 3000mm, said flow-regulating portion being attached to the end surface of the housing.

9. The device of claim 8, wherein a hydrophobic filter is provided at a wall surface of the housing.

10. The device of claim 9, wherein an air-venting portion having an air-venting filter, comprising a hydrophobic filter, is provided at an upper stream of the flow-regulating portion.

11. A liquid infusion device comprising:
a bladder assembly including
a tubular outer shaft,
an inner shaft slidably received within the outer shaft,
a bladder made of elastic material placed outside the outer shaft and inner shaft, one end of said bladder being tightly fixed to the outer shaft and another end of said bladder being fixed to the inner shaft, said inner shaft sliding within the outer shaft based upon an amount of liquid in the bladder, and
an inlet/outlet portion communicated to one end of the outer shaft opposite to an end wherefrom the inner shaft is inserted, said inlet/outlet portion allowing a liquid into and out of said bladder;
a housing containing the bladder portion, the inlet/outlet portion being communicated to the outer shaft on the end surface of housing; and
a flow-regulating portion including a spring-shaped pipe having an inner diameter of 10 to 500 $\mu$m, said flow-regulating portion being attached to the end surface of the housing.

12. The device of claim 11, wherein a hydrophobic filter is provided at a wall surface of the housing.

13. The device of claim 12, wherein an air-venting portion having an air-venting filter, comprising a hydrophobic filter, is at an upper stream of the flow-regulating portion.

* * * * *